United States Patent [19]

Zaiger et al.

[11] Patent Number: Plant 6,408

[45] Date of Patent: Nov. 22, 1988

[54] NECTARINE TREE "ZEE GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 941,724

[22] Filed: Dec. 12, 1986

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree which is of large size, vigorous, upright in growth, and a productive and regular bearer of large, firm, yellow flesh, clingstone fruit having a high degree of attractive red skin color. The fruit is further characterized by relatively uniform ripening throughout the tree, holding firm on the tree for 8–10 days after picking ripe, storing for 30 days in cold storage and maintaining 5–7 days of shelf life with good flavor and eating quality.

1 Drawing Sheet

ORIGIN OF THE VARIETY

The new and distinct variety of nectarine tree was originated by us in the experimental orchard located near Modesto, Calif. as a second generation seedling of a cross between two selected seedlings, both unnamed. The maternal parent was a seedling selection from open pollinated Red Grand Nectarine (U.S. Plant Pat. No. 1,060) seedlings and the pollen parent was a second generation seedling selection of seedlings grown from a cross between Sun Grand Nectarine (U.S. Plant Pat. No. 974) and Merrill Gem Peach (U.S. Plant Pat. No. 868). The new selection was grown and maintained under careful observation during which time we recognized its desireable characteristics described above and selected the variety for asexual reproduction in contemplation of potential commercialization.

ASEXUAL REPRODUCTION OF THE VARIETY

The present variety of nectarine tree was asexually propagated in the experimental orchard, located near Modesto, Calif., by budding, and such reproductions ran true to the original tree and its fruit in all respects.

SUMMARY OF THE VARIETY

The present variety of nectarine tree is of large size, vigorous, upright in growth and a productive and regular bearer of large, yellow flesh, clingstone fruit with good flavor and eating quality. The fruit is further characterized by relatively uniform ripening throughout the tree, holding firm on the tree for 8–10 days after picking ripe, having a high degree of red skin color, firm flesh and good storage and shipping quality.

The present variety of nectarine is further characterized by maturing 3–5 days before Late Le Grand Nectarine (U.S. Plant Pat. No. 1,035), and in comparison to the Late Le Grand Nectarine, the fruit of the present variety is more uniform in ripening throughout the tree, has greater storage life and a higher degree of attractive red skin color.

BRIEF DESCRIPTION OF THE PHOTOGRAPHS

The accompanying photographs show reproductions in color, of typical specimens of the foliage and fruit of the new variety of nectarine tree; such illustrations being of the upper and lower surfaces of the leaves and a fruit divided in the suture plane to reveal flesh coloration and showing a stone remaining in place. The illustrations were taken shortly after being picked at maturity (shipping ripe) and the colors are as nearly true as reasonably possible in a color representation of this type.

DESCRIPTION OF THE VARIETY

The botanical details of this new and distinct variety of nectarine tree, as based upon observations of specimens grown at Modesto, Calif., with color terminology (except those in common terms) in accordance with Reinhold color Atlas by A. Korneruf and J. H. Wanscher.

Tree:
- *Size.*—Large.
- *Vigor.*—Vigorous.
- *Form.*—Upright.
- *Density.*—Medium dense.
- *Shape.*—Normally pruned to vase shape.
- *Production.*—Productive.
- *Bearer.*—Regular.

Trunk:
- *Size.*—Medium to large.
- *Texture.*—Medium shaggy.

Branches:
- *Size.*—Medium to large.
- *Texture.*—Medium rough.
- *Lenticels.*—Numerous. Medium to large size.
- *Color.*—Brown to reddish brown.

Leaves:
- *Size.*—Large. Average length — 6½" to 7". Average width — 1¼" to 1½".
- *Form.*—Lanceolate.
- *Margin.*—Serrate.
- *Petiole.*—Medium length. Medium thickness.
- *Glands.*—Reniform. Medium size. Number varies from 2 to 6. Average number 4. Positioned on base of blade and upper portion of the petiole, usually alternate.
- *Color.*—Upper surface — dark green (27-F-7) to (27-F-8). Lower surface — grayish green (28-E-6) to (28-E-7).

Flower buds:
- *Size.*—Medium size.
- *Form.*—Plump.

*Pubescence.*—Pubescent.

Flowers:

*Size.*—Large — showy.

*Bloom period.*—Feb. 28, 1985 to Mar. 9, 1985. Varies slightly with climatic conditions.

*Pollen.*—Present.

*Color.*—Pink.

Fruit:

*Maturity when described.*—Hard ripe.

*Date of first picking.*—Aug. 5, 1985.

*Date of last picking.*—Aug. 15, 1985.

*Size.*—Large. Average diameter axially — 2½" to 2¾". Average transversely in suture plane — 2½" to 2¾".

*Form.*—Usually globose — varies from globose to slightly elongated.

*Suture.*—Distinct — extends from base to apex.

*Cavity.*—Rounded to slightly elongated in suture plane. Average depth — ⅝". Average breadth — 1".

*Base.*—Retuse.

*Apex.*—Usually slight point. Varies from slight point to slight depression.

Skin:

*Thickness.*—Medium.

*Texture.*—Medium.

*Tendency to crack.*—None.

*Down.*—Wanting.

*Color.*—Yellow ground color (3-A-8) to (4-A-8). Red blush covering most of the surface of the fruit, shading from currant red (9-A-8) to cherry red (9-B-8).

Flesh:

*Texture.*—Firm.

*Ripens.*—Even.

*Juice.*—Moderate.

*Flavor.*—Sub-acid to mild.

*Eating quality.*—Good.

*Color.*—Orange yellow (4-A-7) to dark yellow (4-A-8). Slight red coloring (9-B-8) near apex of stone.

Stone:

*Type.*—Clingstone.

*Size.*—Large. Average length — 1 5/16". Average breadth — 1 1/16". Average thickness — ¾".

*Form.*—Ovid.

*Base.*—Mostly straight.

*Apex.*—Acute.

*Sides.*—Nearly equal.

*Surface.*—Irregularly furrowed toward apex — pitted toward base.

*Tendency to split.*—Slight.

*Color.*—Brown (8-C-5) to (8-D-5).

Use: Dessert.

*Market.*—Local and long distance.

Keeping quality: Excellent.

Shipping quality: Good.

The nectarine tree and its fruit herein described, may vary in slight detail due to climatic, soil conditions and cultural practices under which the variety may be grown; the present description being of the variety as grown by us in the experimental orchard located near Modesto, Calif.

We claim:

1. A new and distinct variety of nectarine tree as illustrated and described, characterized by its large size, upright growth and being a regular and productive bearer of large, firm, yellow flesh, clingstone fruit with good eating and shipping quality; and in comparison to Late Le Grand Nectarine (U.S. Plant Pat. No. 1,035), maturing 3–5 days earlier, having a greater degree of attractive red skin color and the ability to store thirty days in cold storage and maintain 5–7 days of shelf life with good flavor and eating quality.

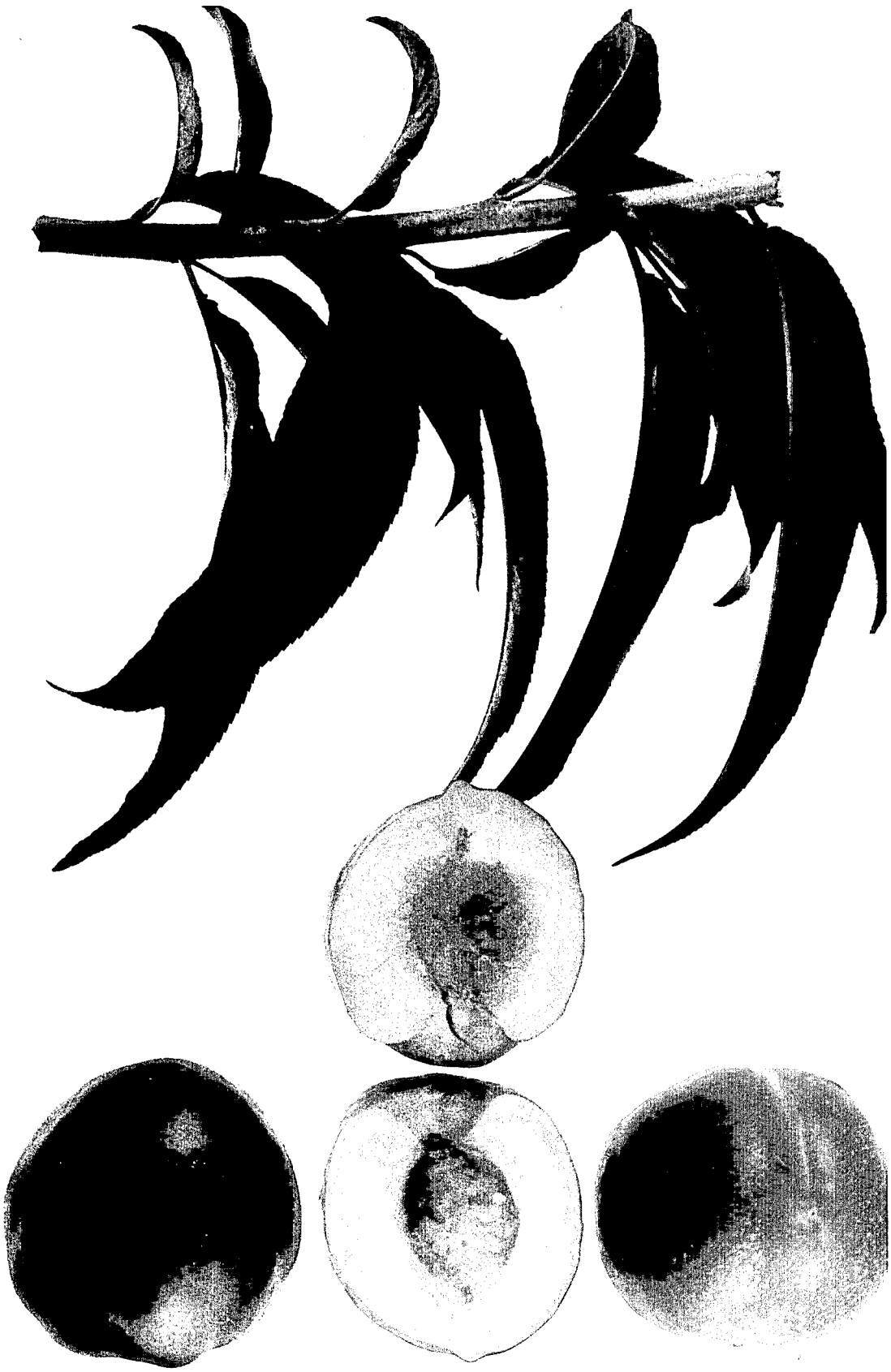

* * * * *